(12) United States Patent
Samuels

(10) Patent No.: US 10,137,018 B2
(45) Date of Patent: Nov. 27, 2018

(54) ENDOVASCULAR ROUTER DEVICE AND METHOD

(76) Inventor: Shaun L. W. Samuels, Coral Gables, FL (US)

( * ) Notice: Subject to any disclaimer, the term of this patent is extended or adjusted under 35 U.S.C. 154(b) by 714 days.

(21) Appl. No.: 12/765,516

(22) Filed: Apr. 22, 2010

(65) Prior Publication Data
US 2010/0292772 A1    Nov. 18, 2010

Related U.S. Application Data

(60) Provisional application No. 61/214,449, filed on Apr. 23, 2009.

(51) Int. Cl.

| | |
|---|---|
| *A61F 2/07* | (2013.01) |
| *A61F 2/856* | (2013.01) |
| *A61F 2/954* | (2013.01) |
| A61F 2/06 | (2013.01) |
| A61F 2/848 | (2013.01) |
| A61F 2/90 | (2013.01) |

(52) U.S. Cl.
CPC ............ *A61F 2/954* (2013.01); *A61F 2/07* (2013.01); *A61F 2/90* (2013.01); *A61F 2002/061* (2013.01); *A61F 2002/065* (2013.01); *A61F 2002/072* (2013.01); *A61F 2002/075* (2013.01); *A61F 2002/8486* (2013.01); *A61F 2250/0003* (2013.01); *A61F 2250/0039* (2013.01)

(58) Field of Classification Search
CPC ....... A61F 2/062; A61F 2002/061; A61F 2/95
USPC ............... 623/1.11, 1.12, 1.23, 1.25
See application file for complete search history.

(56) References Cited

U.S. PATENT DOCUMENTS

| 4,923,464 A | * | 5/1990 | DiPisa, Jr. ................. A61F 2/95 606/195 |
| 5,151,105 A | * | 9/1992 | Kwan-Gett .................. 623/1.32 |
| 5,423,851 A | | 6/1995 | Samuels |
| 5,562,724 A | * | 10/1996 | Vorwerk ................... A61F 2/07 606/195 |

(Continued)

OTHER PUBLICATIONS

PCT International Search Report and Written Opinion of the International Searching Authority for International Application No. PCT/US2010/032059, dated Jun. 28, 2010.

*Primary Examiner* — Katherine Rodjom
(74) *Attorney, Agent, or Firm* — The Petruzzi Law Firm; James D. Petruzzi

(57) ABSTRACT

A router device is a intraluminal prosthesis which is used in the repair of aneurysms and other diseases of the aorta. The device also has applications in other vascular beds. The device incorporates an inflatable cuff or sequence of cuffs at one end for fixation and sealing. This cuff may be placed proximal to branch vessels of the aorta. Attached to the cuff is a tubular graft consisting of a generally cylindrical graft material. The graft material may contain one or more fenestrations, intended to align with branch vessels as they emerge from the parent vessel, the aorta in the preferred embodiment. The device features a deliberate taper of its diameter as the device crosses the area of branch vessels. This taper brings the diameter of the graft material to a lesser diameter than that of the parent vessel, leaving a deliberate and distinct space between the device and the wall of the vessel. This space allows more easily achieved engagement of the branch vessels with stents using standard catheterization techniques.

34 Claims, 17 Drawing Sheets

(56) References Cited

U.S. PATENT DOCUMENTS

| | | | | |
|---|---|---|---|---|
| 5,653,743 A * | 8/1997 | Martin | | A61F 2/07 606/153 |
| 5,693,088 A * | 12/1997 | Lazarus | | A61F 2/07 606/195 |
| 5,848,964 A | 12/1998 | Samuels | | |
| 5,908,435 A | 6/1999 | Samuels | | |
| 5,947,995 A | 9/1999 | Samuels | | |
| 6,007,575 A * | 12/1999 | Samuels | | 623/1.15 |
| 6,159,230 A | 12/2000 | Samuels | | |
| 6,428,565 B1 | 8/2002 | Wisselink | | |
| 6,551,350 B1 * | 4/2003 | Thornton | | A61F 2/06 606/198 |
| 7,520,890 B2 | 4/2009 | Phillips | | |
| 8,206,427 B1 * | 6/2012 | Ryan | | A61F 2/07 623/1.11 |
| 2001/0027338 A1 * | 10/2001 | Greenberg | | 623/1.13 |
| 2002/0058986 A1 * | 5/2002 | Landau | | A61F 2/064 623/1.13 |
| 2003/0093145 A1 * | 5/2003 | Lawrence-Brown et al. | | 623/1.21 |
| 2004/0059406 A1 * | 3/2004 | Cully | | A61F 2/07 623/1.11 |
| 2004/0106972 A1 * | 6/2004 | Deaton | | A61F 2/07 623/1.1 |
| 2004/0138734 A1 * | 7/2004 | Chobotov | | A61F 2/954 623/1.11 |
| 2005/0102018 A1 * | 5/2005 | Carpenter et al. | | 623/1.11 |
| 2005/0171599 A1 * | 8/2005 | White | | A61F 2/064 623/1.36 |
| 2006/0025855 A1 * | 2/2006 | Lashinski et al. | | 623/2.1 |
| 2006/0074481 A1 * | 4/2006 | Vardi | | A61F 2/07 623/1.36 |
| 2007/0219621 A1 * | 9/2007 | Hartley et al. | | 623/1.13 |
| 2007/0299497 A1 * | 12/2007 | Shaolian | | A61F 2/07 623/1.11 |
| 2008/0262595 A1 * | 10/2008 | Chu | | A61F 2/064 623/1.13 |
| 2008/0312732 A1 * | 12/2008 | Hartley | | A61F 2/07 623/1.13 |
| 2010/0137966 A1 * | 6/2010 | Magnuson | | A61F 2/95 623/1.11 |

* cited by examiner

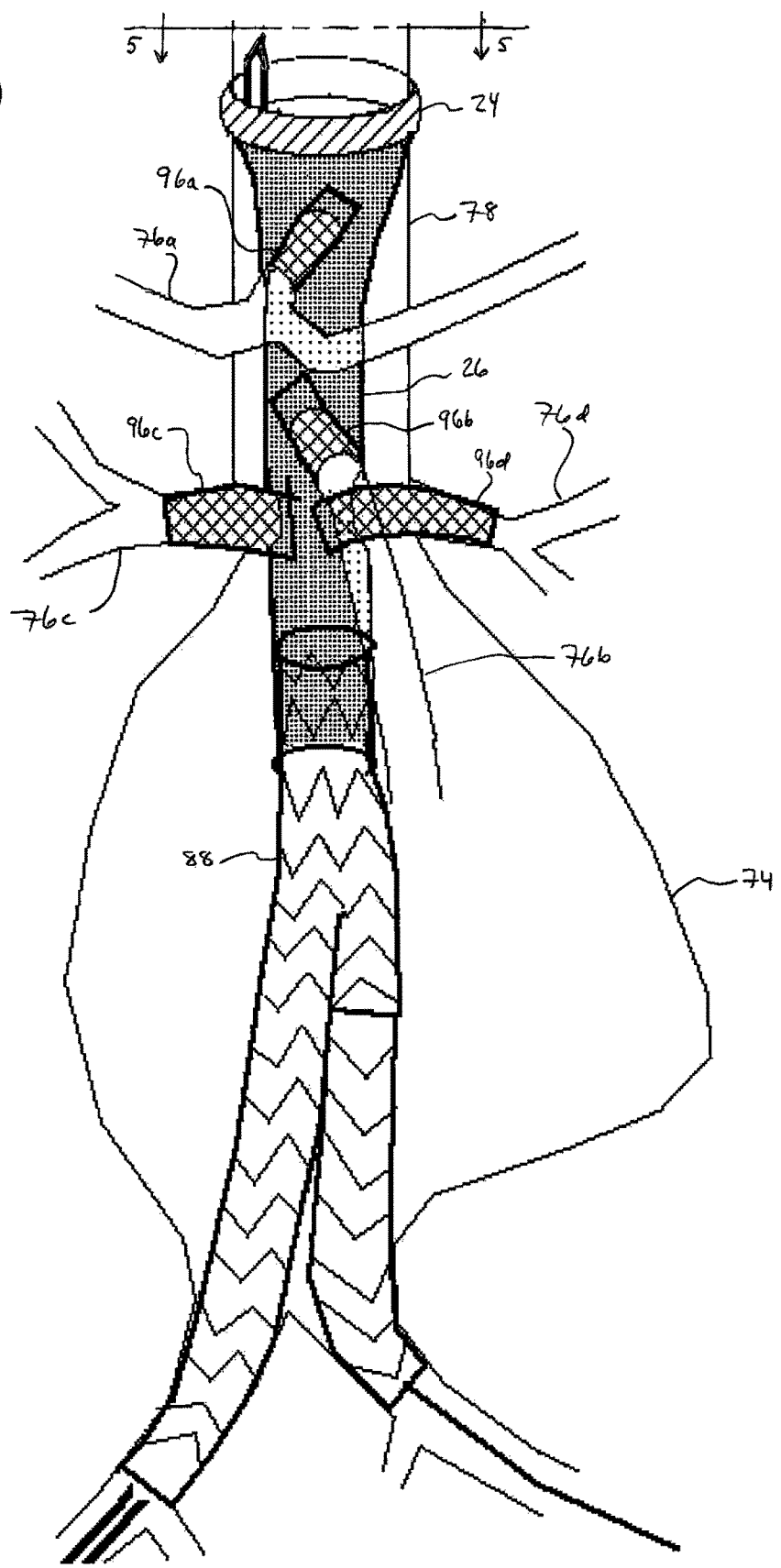

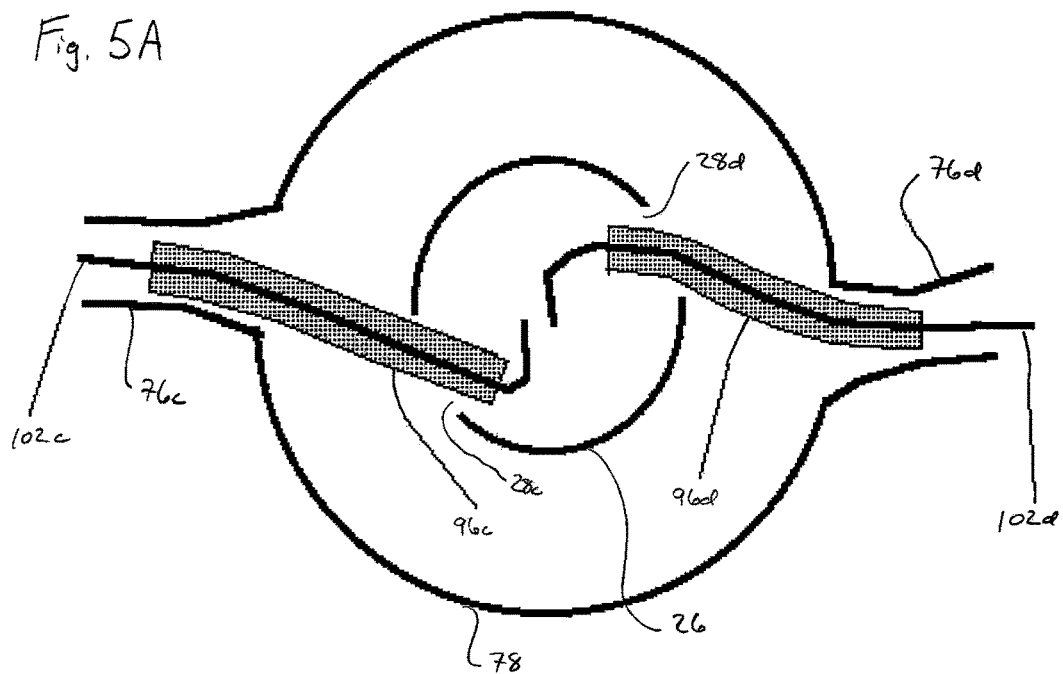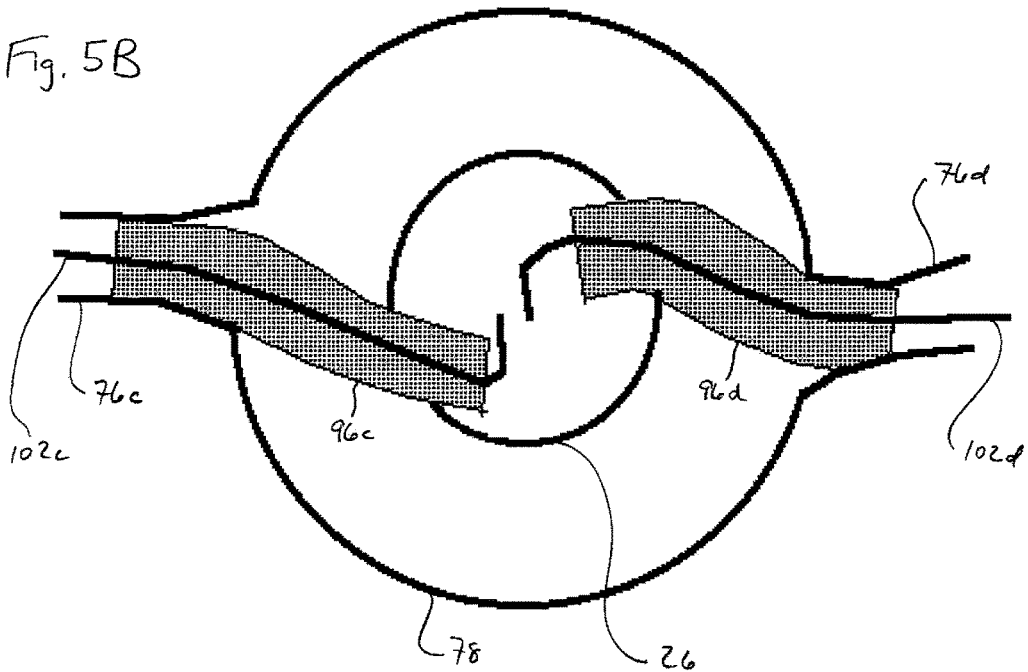

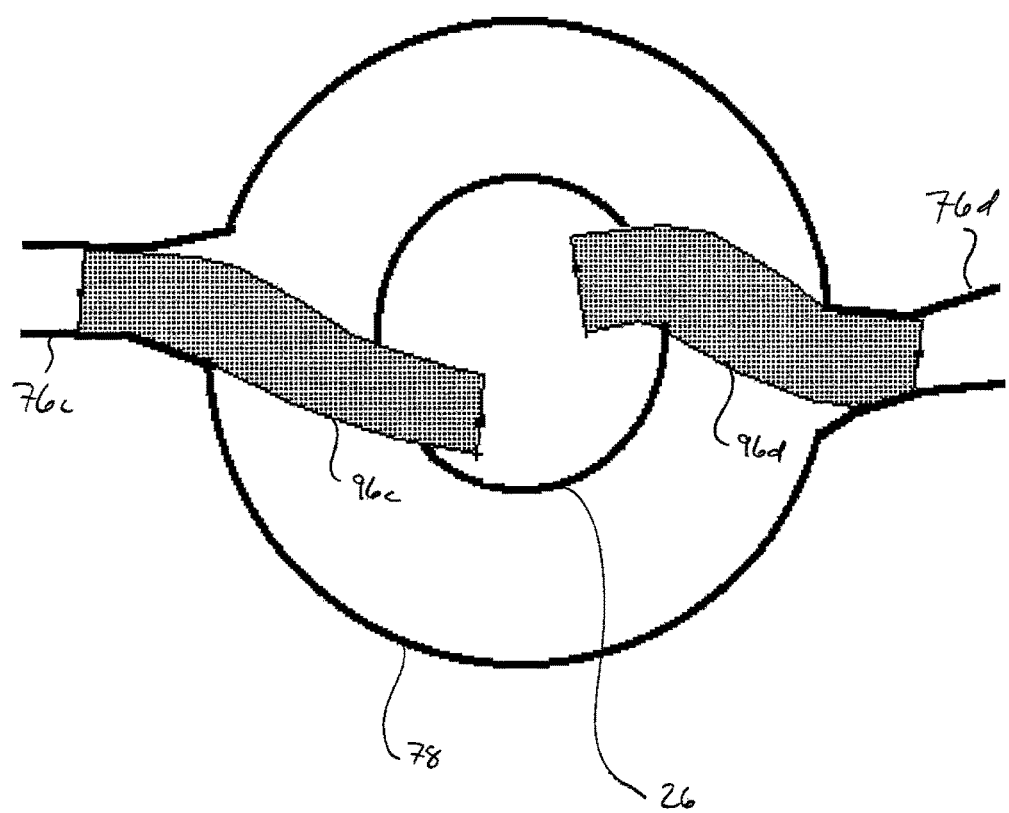

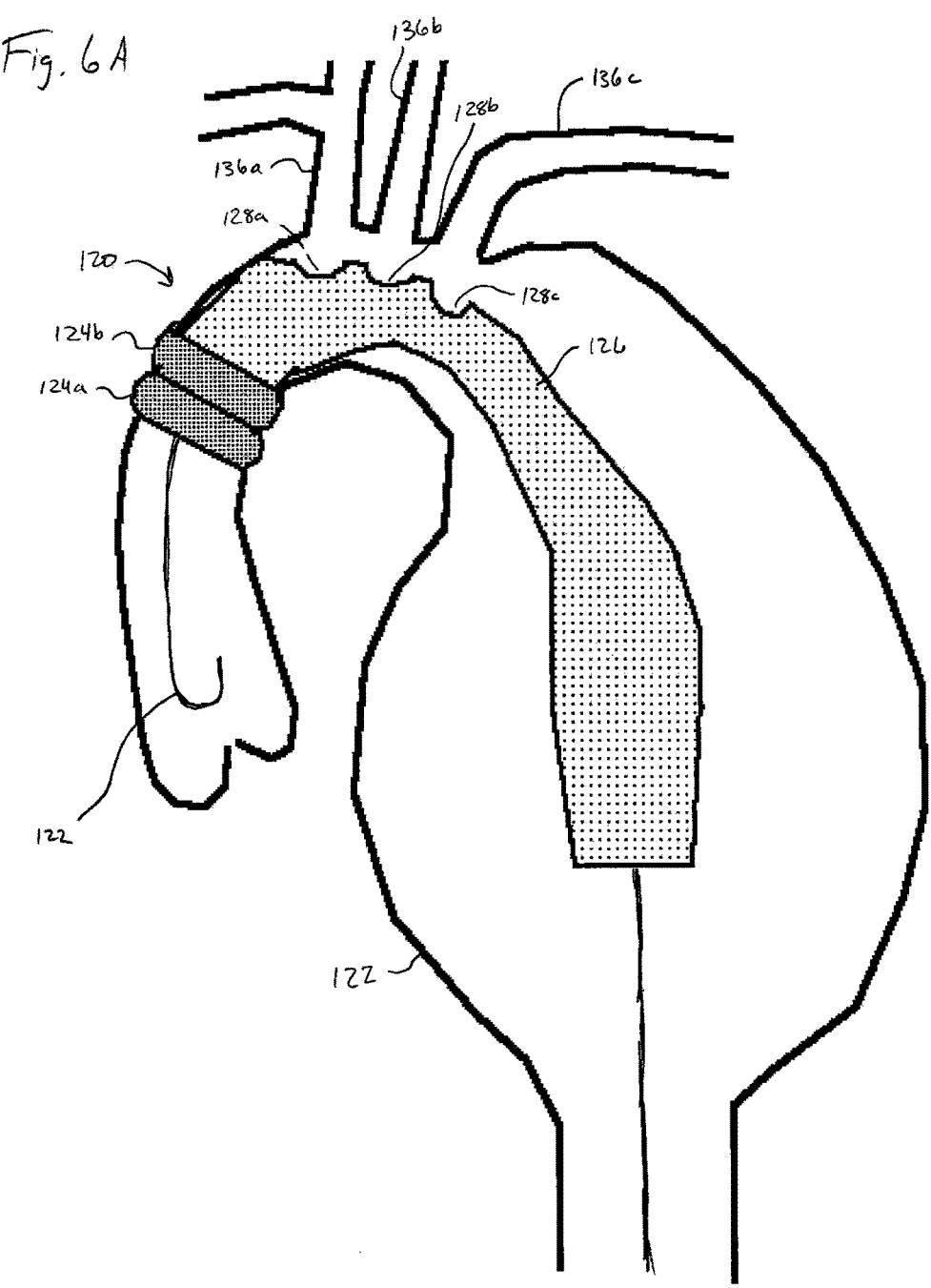

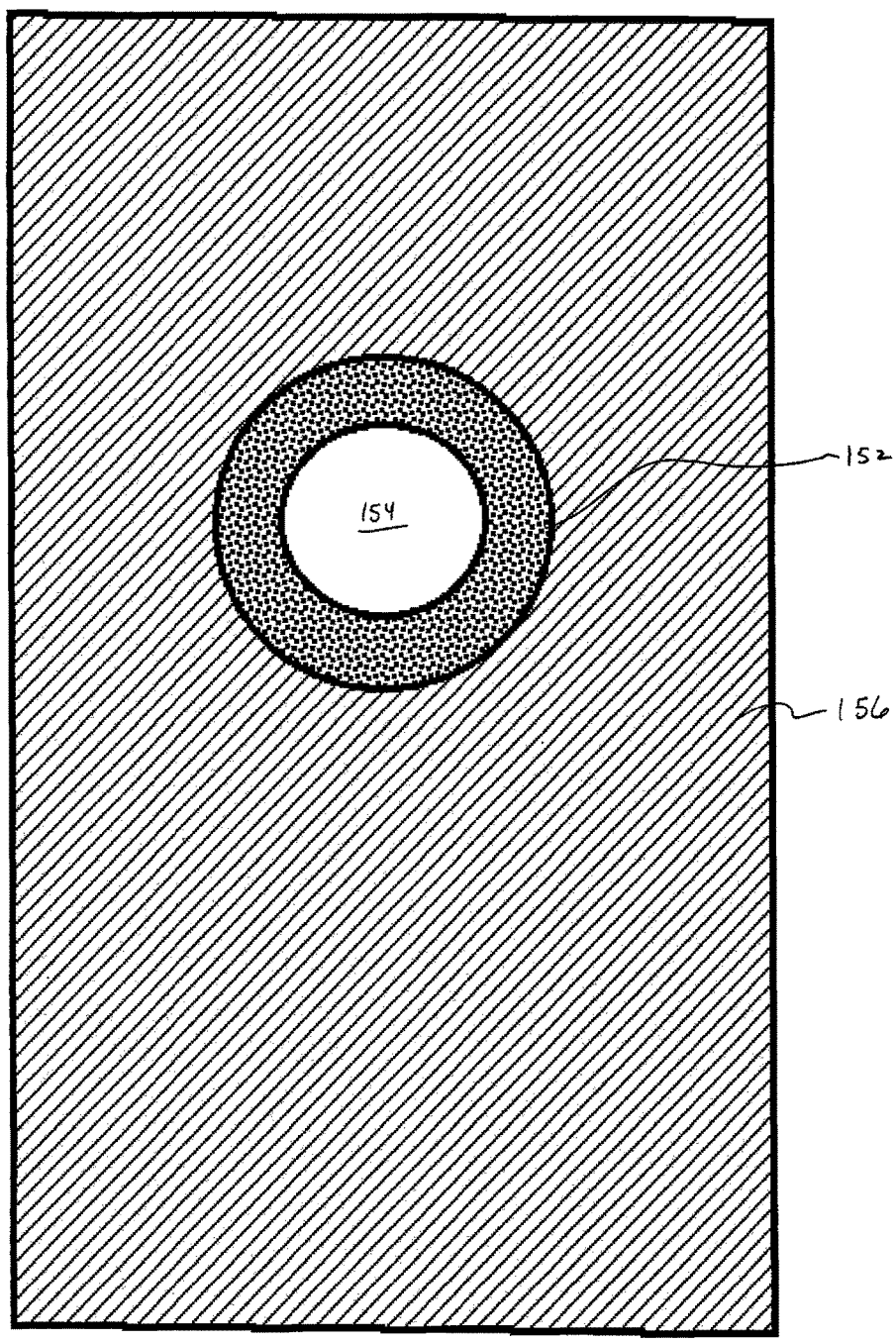

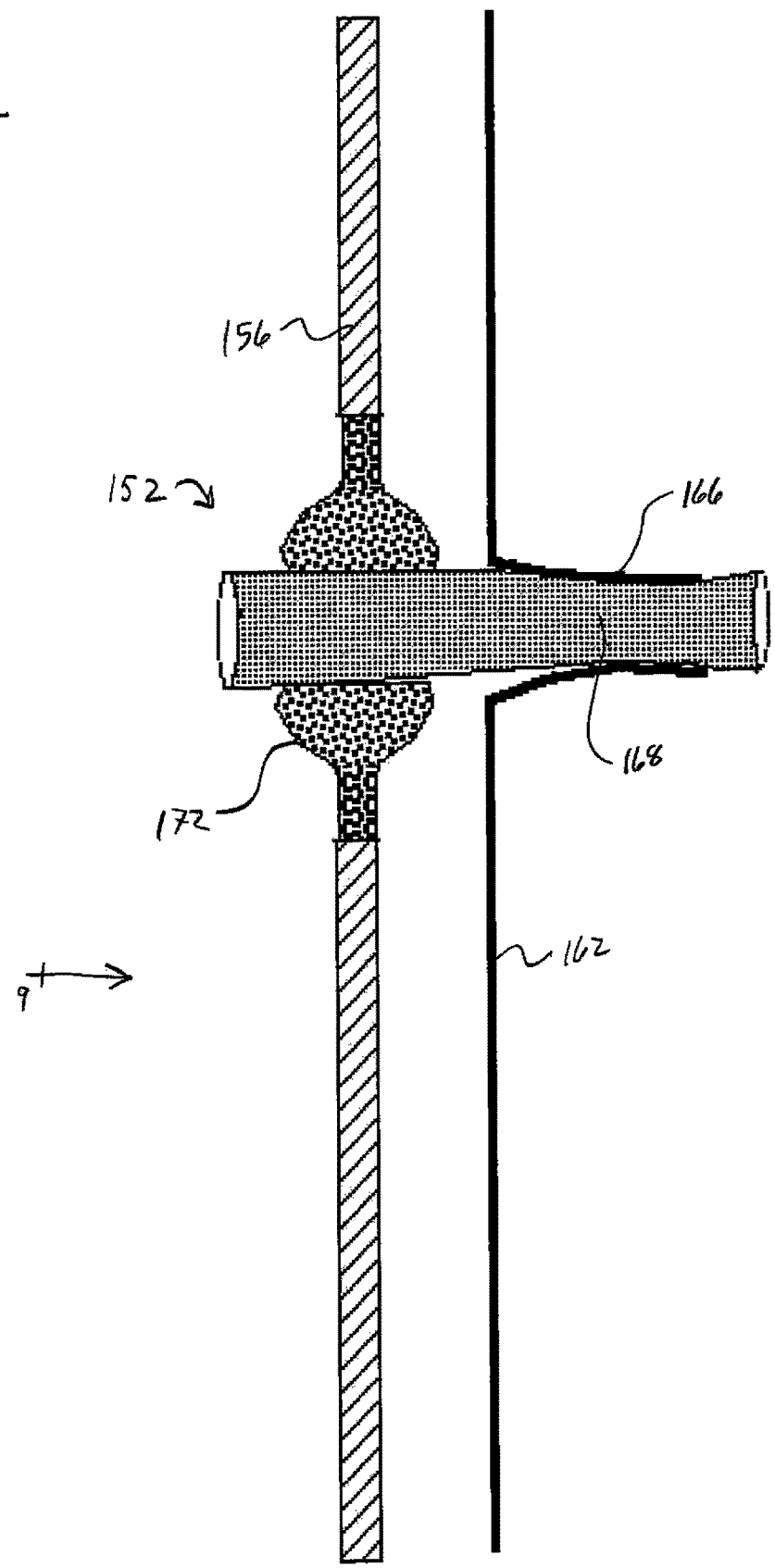

ENDOVASCULAR ROUTER DEVICE AND METHOD

CLAIM OF PRIORITY

This application claims priority from U.S. Provisional Patent Application Ser. No. 61/214,449, filed Apr. 23, 2009.

FIELD OF THE INVENTION

This invention relates generally to an intra-luminal prosthesis for repair of body conduits. More specifically, the invention relates to an intra-arterial prosthesis to aid in the repair of an abnormal vessel.

BACKGROUND

Various tubular vessel structures within the human body, such as the biliary duct system, excretory system and vascular system, may deteriorate so that medical repair is necessary. For example, aortic aneurysms are abnormal ballooning out of the wall of the vessel, and put a person at risk of death from rupture of the aneurysm. These aneurysms most commonly involve the abdominal aorta just below the level of the arteries that supply the kidneys. The second most common location for such aneurysms is in the thoracic aorta, adjacent to the major branches which supply the head and arms.

Endovascular devices for repairing such aneurysms are known in the art. Several have been commercialized, including those made by Cook Vascular Incorporated of Vandergrift, Pa., W.L. Gore & Associates Inc. of Flagstaff, Ariz., Medtronic Inc. of Minneapolis, Minn. and Endologix, Inc. of Irvine, Calif. Such prior art devices are generally introduced through a vessel in the groin and tracked over a guidewire. The devices are typically introduced in a constrained condition, so as to allow access through the relatively smaller groin artery.

The prior art devices have significant similarities in terms of their overall structure. They are usually modular, in which a "main body" is introduced as one device, with a method of fixation and sealing incorporated into the proximate component, and an "ipsilateral limb", which extends into the iliac artery. There is a "gate" as part of the main body, which is then cannulated from the contralateral groin so that a "contralateral limb", a tubular stent-graft component, may be deployed to complete the two-piece endograft system.

In the thoracic aorta, the design is generally simpler, as the aorta does not branch over the course of the descending thoracic aorta. Hence there is only a single, tubular component to the endograft device.

In both the abdominal and thoracic aorta, the primary anatomic limitation to the success of aneurysm exclusion is the proximity of the major branch vessels to the aneurysm itself. The interval between the last major branch vessel and the aneurysm is referred to as the "neck." Prior art devices generally specify in their Instructions For Use (IFU's) a minimum neck length for which each device is approved for use. Adequate neck length is critical for achieving a seal between the device and the normal aortic wall. If this length is too short, there may be insufficient wall contact to effectively exclude the aneurysm, leading to persistent flow in the aneurysm, or "endoleak".

Unfortunately, the necks of both abdominal aortic aneurysms (AAA's) and thoracic aortic aneurysms (TAA's) are often too short for reliably successful endograft placement. In such cases, open surgical repair may be the only option. Many of the patients with AAA or TAA, however, have other conditions that make them very poor open surgical candidates, and hence no good option is available for their treatment.

In the past several years, many experimental techniques have been developed in an attempt to remedy this problem. These fall primarily into the categories of branched endografts and "fenestrated" endografts. Each involves a modified stent graft, with either holes created to align with the branch vessels (fenestrated), or pre-attached branch limbs which engage the branch vessels. In order to ensure proper alignment of these devices, extremely elaborate systems of guidewires are employed to pre-engage the branch vessels. This is a complex process which is beyond the skill set of many endovascular specialists, and makes such procedures difficulty to perform, lengthy, and more likely to produce complications.

In addition, all of the currently available endograft systems depend on a metallic endoskeleton for fixation, which is achieved through continuously outward frictional force generated by the spring-like metal. The metal, however, is relatively stiff, and hence does not conform well to the aorta when there is significant tortuosity of the vessel, or angulation of the vessel segments. Furthermore, the endografts fully supported by this metallic endoskeleton cannot be repositioned once deployed. Hence any malalignment of the endograft with side branches cannot be corrected, and this constitutes a potentially catastrophic limitation. For these reasons, adoption of fenestrated endografts has been extremely limited, and this has greatly limited the options available to a large subgroup of patients with life-threatening aneurysms.

BRIEF DESCRIPTION OF THE DRAWINGS

FIGS. 4A-4D are cross-sectional views of an abdominal aortic aneurysm and branch arteries with the router device and catheter of FIGS. 1-3B, a endograft device and stents being deployed therein in accordance with an embodiment of the method of the present invention;

FIGS. 5A-5C are cross-sectional views of the aorta and renal arteries of FIGS. 4A-4D taken along line 5-5 of FIG. 4D showing the positioning and attachments of stents to the router device in accordance with an embodiment of the method of the present invention;

FIGS. 6A-6C are cross-sectional views of a thoracic aortic aneurysm and branch arteries with an embodiment of the router device of the present invention, an endograft device and stents being deployed therein in accordance with an embodiment of the method of the present invention;

FIG. 7 is a side elevational view of a tubular graft wall of an embodiment of the router device of the present invention with a malleable portion surrounding a fenestration;

FIGS. 8A-8C are cross-sectional views of the aorta showing the positioning and attachments of a stent to the fenestration of the router device of FIG. 7 in accordance with an embodiment of the method of the present invention;

DETAILED DESCRIPTION OF EMBODIMENTS

The present invention is directed towards an intraluminal prosthesis for aiding in the repair of an abnormal tubular vessel of a patient. In preferred embodiments, described below, the present invention is used in the repair of aortic aneurysms.

Figure 1:
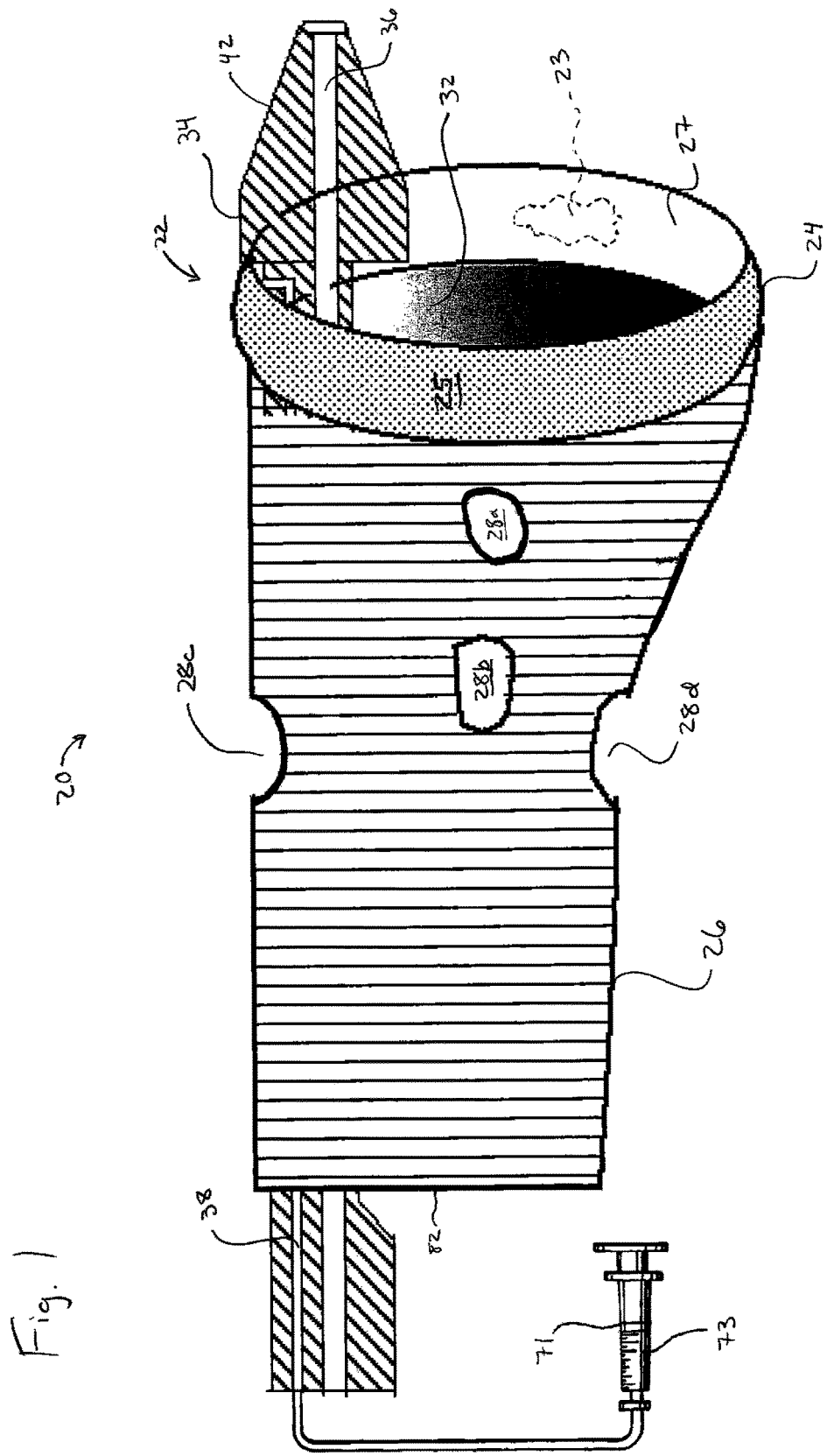
FIG. 1 is a perspective view of an embodiment of the router device of the present invention with a cross-sectional view of the deployment catheter attached to the router device.

With reference to FIG. 1, a preferred embodiment of the router device is indicated in general at 20. The device 20, shown in its inflated and deployed configuration, consists of a generally tubular structure, having a proximal or first end, indicated in general at 22, provided with an arrangement for affixing the device to the interior surface of the artery. In the preferred embodiment, this fixation consists of an inflatable element, preferably in the form of an inflatable cuff 24 incorporated into the first end of the device.

The cuff 24 is preferably composed of bioinert, polymeric plastic, and, as illustrated in FIG. 1, is of cylindrical shape and defines a comparatively large central opening 32 surrounded by the relatively thin inflatable element (the inflatable cuff 24). An annular inflatable chamber, a section of which is indicated in phantom at 23 in FIG. 1, is defined between the outer and inner surfaces of the cuff, indicated at 25 and 27, respectively. When deployed, the inflatable cuff 24 is disposed transversely within a vessel lumen, juxtaposed circumferentially to the interior surface of the vessel. The cuff preferably includes a friction-enhancing outer surface 25 which may include, for example, circumferential ridges and/or a course texture formed, for example, by a combination of raised and lowered surface portions. In addition, it may be desirable in some applications to provide the cuff with an outer surface that promotes tissue ingrowth. Such a surfaced material could include, for example, TEFLON.

While one cuff is illustrated in FIG. 1, multiple inflatable cuffs may alternatively be provided. In addition, the cuff(s) may take on a variety of configurations and, as described below, may be inflated and deflated, before a final inflation in the desired location is performed. A suitable construction and use of the cuff is disclosed in commonly owned U.S. Pat. No. 6,007,575, the contents of which are hereby incorporated herein by reference.

The router device also features a generally tubular graft 26 to which the cuff is attached at the proximal end. The tubular graft is preferably constructed from a biocompatible synthetic material, such as DACRON or TEFLON, but is not limited to these two materials. For example, the tubular graft 26 could be made of polyester or polytetrafluoroethylene or any other biocompatible material. In addition, as explained in greater detail below, the tubular graft is provided with a number of fenestrations 28a-28d. While four generally round fenestrations are illustrated in FIG. 1, it will be apparent that the tubular graft may be provided with a greater or lesser number of fenestrations and fenestrations of different shapes and sizes.

The tubular graft at the proximal or first end 22 is of a diameter equal to or slightly greater than the diameter of the non-aneurysmal aortic wall proximate to the aneurysm and branch vessels. The inflatable cuff is intended for positioning proximate to the major branch vessels in either a abdominal aortic aneurysm (AAA) or a thoracic aortic aneurysm (TAA). In the case of a AAA, this proximate location may be above the renal arteries, or above the superior mesenteric artery and renal arteries, or, lastly, above the celiac axis, superior mesenteric artery, and renal arteries. In each of these cases, the construction of the tubular graft component of the device differs: there is one fenestration for each branch vessel. In the case of a suprarenal fixation, therefore, there are two fenestrations; for a supramesenteric fixation, there are three: one for the superior mesenteric artery, and one for each renal artery. There are four fenestrations for the supraceliac fixation, with the last fenestration corresponding to the origin of the celiac axis.

The positions of the fenestrations (28a-28d of FIG. 1), which are placed as part of the fabrication process of the device, are preferably determined by previously obtained imaging, usually consisting of a computed tomography (CT) scan. Such scans identify very precisely the location of the major branch vessels. The data set is made available to the fabricator of the device, and the fenestrations located accordingly. Alternatively, a standard set of fenestrations may be incorporated into a set of non-customized devices, based on general anatomic data which encompass a certain, presumably large percentage of the population.

The tubular graft 26 is preferably of a generally tapered configuration, with the diameter of the tubular graft decreasing as the distance from the inflatable cuff increases. The average diameter of the fenestrated section is less than that of the adjacent aortic wall. This is the case whether or not the segment of aorta from which the branch vessels originate is aneurysmal or not.

Figure 2A:
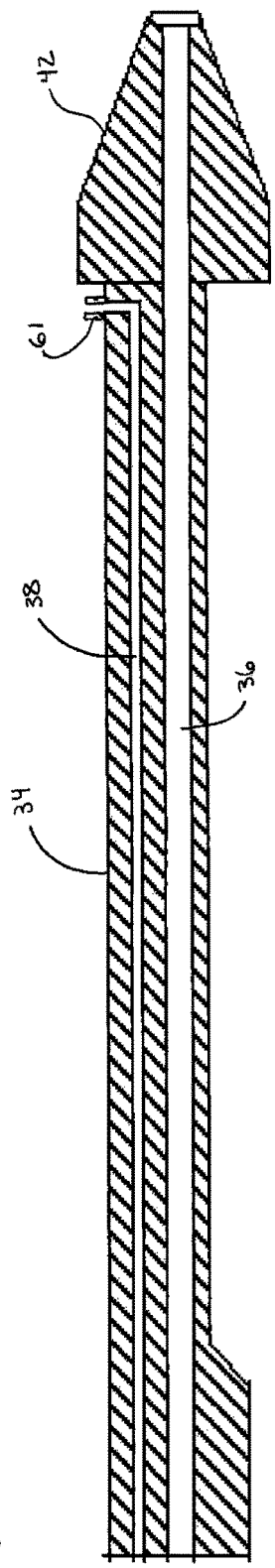
FIGS. 2A and 2B are cross-sectional views of the deployment catheter of FIG. 1 with the router device removed and with the router device in a collapsed condition over the catheter, respectively.
Figure 2B:
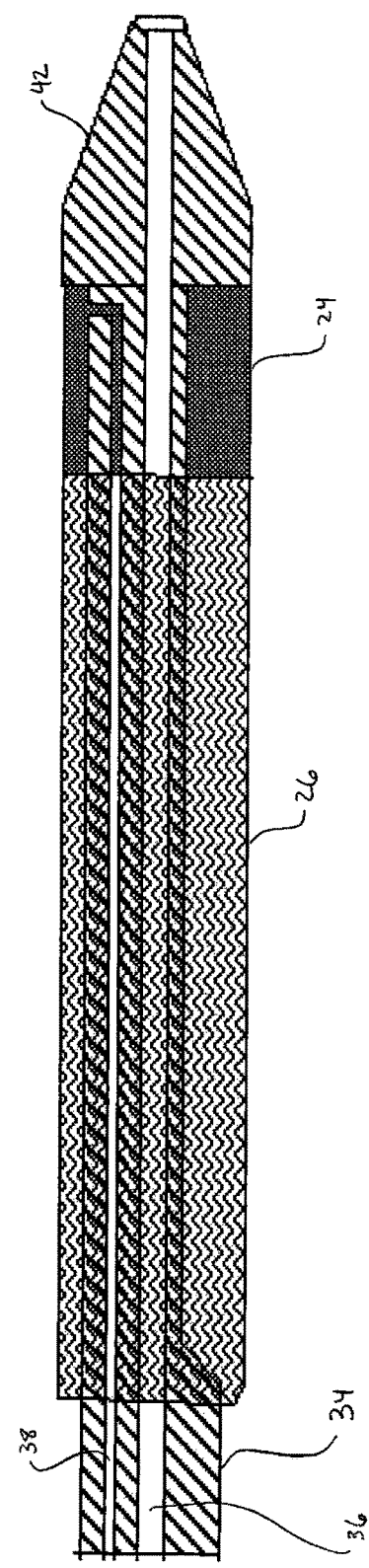

As illustrated in FIGS. 1 and 2B, the inflatable cuff is attached by its inner surface to a deployment catheter 34. The deployment catheter 34 without the inflatable cuff attached is illustrated in FIG. 2A. The catheter 34 is preferably constructed of a polymeric plastic which is bioinert and features a central or guidewire lumen 36 and an inflation lumen 38.

As illustrated in FIGS. 1-2B, guidewire lumen 36 passes through the center of catheter 34, coaxial with the longitudinal axis of the catheter, and is preferably of sufficient diameter to accommodate a guidewire of at least 0.035 inch diameter. The guidewire lumen 36 opens into a port affixed at the proximal end of catheter 34, which remains outside of the patient's body. Guidewire lumen 36 is preferably of consistent general diameter throughout its length.

The distal portion of catheter 34 undergoes a concentric gentle tapering to a size only slightly larger than guidewire lumen 36 at its tip 42.

The inflation lumen, indicated at 38 in FIGS. 1-2B, is disposed parallel to the guidewire lumen 36, and is used for inflation and deflation of cuff 24. This lumen may be of any size that allows cuff 24 to be easily inflated or deflated and is generally consistent diameter throughout the length of catheter 34. As shown in FIG. 1, one end of inflation lumen 38 terminates at a junction with cuff 24 so that inflation lumen 38 and cuff 24 are in fluid communication with one another. The other end of inflation lumen 38 emerges from the catheter 34 at a location external to the body of the patient.

Figure 3B:
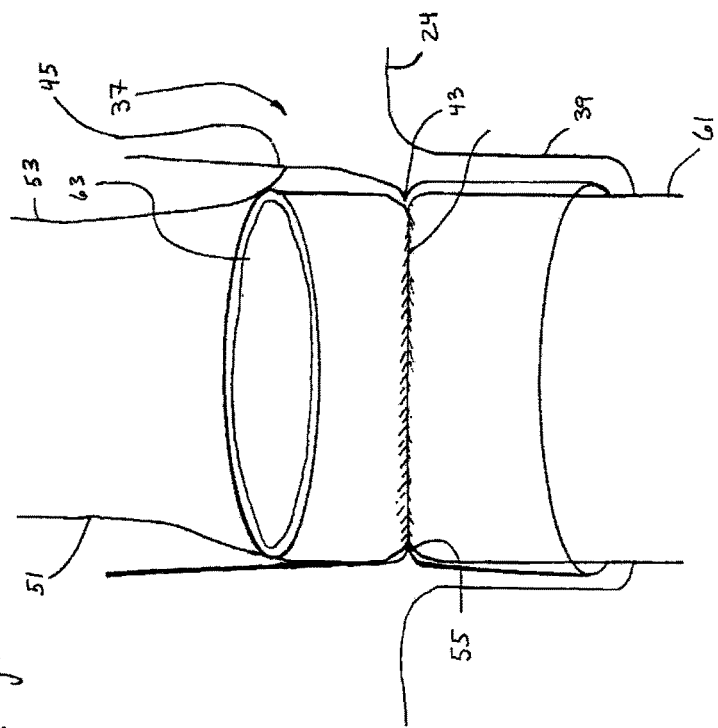
FIGS. 3A and 3B are enlarged perspective views of an embodiment of the inflation port and valve of the inflatable cuff of FIG. 1 and the inflation stem of the catheter of FIG. 2A with the stem disengaged from the port and valve and the stem engaging the port and valve, respectively.
Figure 3A:
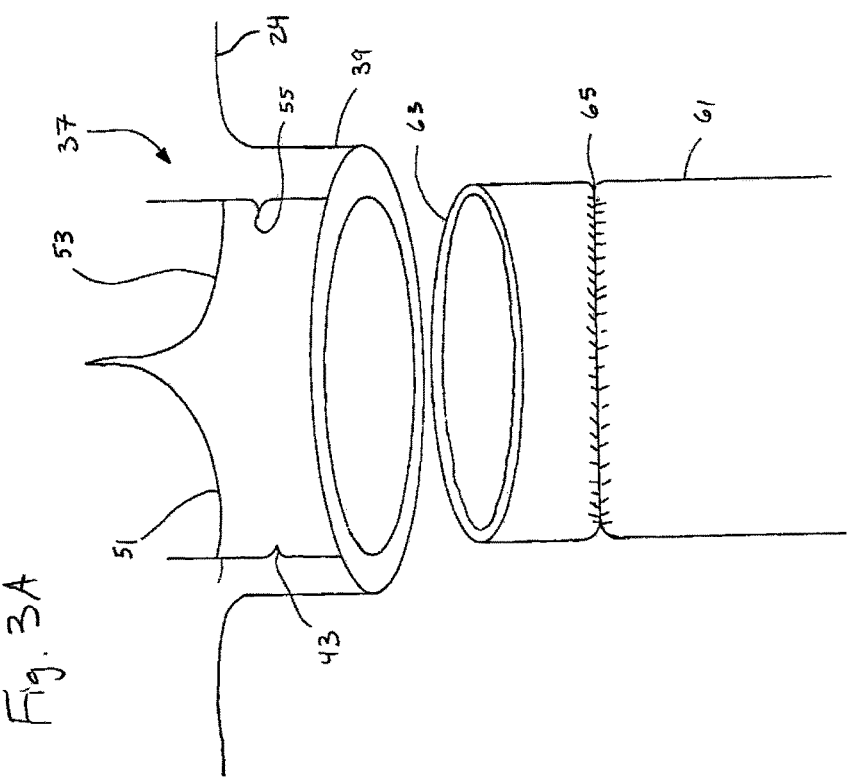

The cuff 24 includes a valve, indicated generally at 37 in FIGS. 3A and 3B, which is integral with inflation port 39 of cuff 24. Preferably, valve 37 combines a breakaway valve 43 with a "duck bill" or "mitre" valve 45. Mitre valve 45 features opposing leaflets 51 and 53 which are constructed of a non-elastomeric, biologically inert material. Breakaway valve 43 features a circumferential rim 55 formed upon the interior surface of inflation port 39. As illustrated in FIG. 2A, catheter 34 is provided with an inflation stem 61 having a passage that is in fluid communication with the inflation lumen. As illustrated in FIGS. 3A and 3B, inflation stem 61 features mating end 63 and circumferential notch 65. As shown in FIG. 3B, when inflation stem 61 is in an engaged configuration with valve 37, mating end 63 separates the opposing leaflets 51 and 53 of mitre valve so that cuff 24 may be inflated or deflated. When in this configuration, again as shown in FIG. 3B, the circumferential notch 65 of the inflation stem 61 engages the circumferential rim 55 so as to secure inflation stem 61 within inflation port 39.

Referring to FIGS. 3A and 3B, once cuff 24 has been inflated to the desired level, a sharp tug on the catheter 34, and thus inflation stem 61, in a direction away from inflation port 39 causes circumferential notch 65 and circumferential rim 55 to disengage. This allows easy withdrawal of mating end 63 from mitre valve 45 and inflation port 39. Upon withdrawal of the mating end 63 of inflation stem 61, as shown in FIG. 3A, opposing leaflets 51 and 53 of mitre valve 45 close to seal the inflated cuff 24.

Alternative valve arrangements known in the art may be substituted for the valve 37 of FIGS. 3A and 3B.

Referring back to FIG. 1, cuff 24 is inflated by way of an inflation syringe 71 with an inflation material 73. The inflation material could be a saline-based fluid or a material that contains a photo-activated or heat-activated hardening agent or any hardening agent that hardens over time. Typically, the inflation syringe 71 is mounted in a screw-feed pressure generating device provided with a manometer in order to accurately gauge inflation pressures. After cuff 17 has been installed and inflated, the material 73 hardens over time to permanently affix router device within the tubular structure of the body.

FIGS. 4A-4D and 5A-5C illustrate the steps to be performed in deploying the aortic router device of FIG. 1 to treat an abdominal aortic aneurysm in the accordance with an embodiment of the method of the present invention.

Figure 4A:
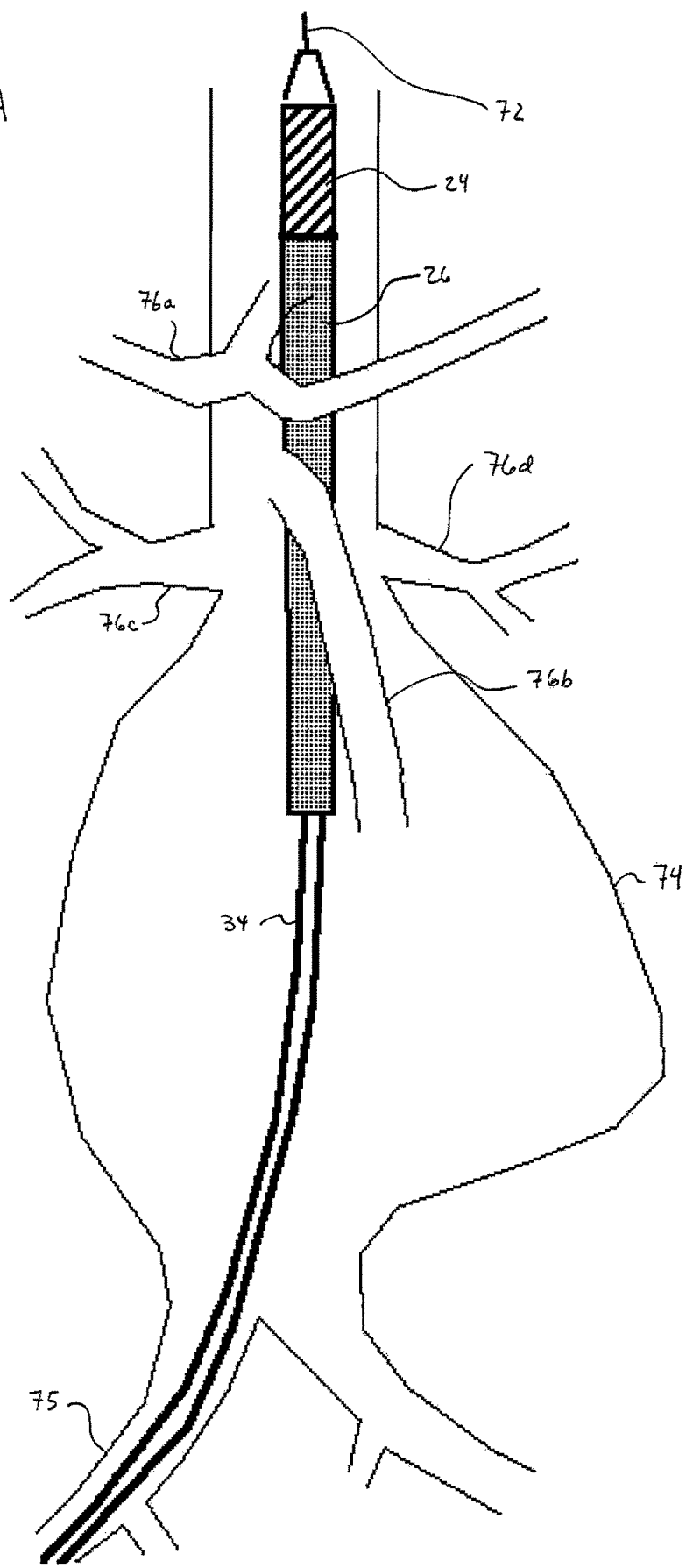

As illustrated in FIG. 4A (and FIG. 2B), the inflatable cuff 24 and tubular graft 26 are collapsed around the catheter 34 behind catheter tapered portion 42. Referring to FIG. 4A, a guide wire 72 is initially fed from outside of the patient's body, through an incision into the groin artery 75 and finally through the aortic artery and past the aneurysm 74. The absence of a metal endoskeleton allows the overall size of the router device to be reduced, and hence there is the potential to introduce it through a smaller catheter delivery system.

Figure 4B:
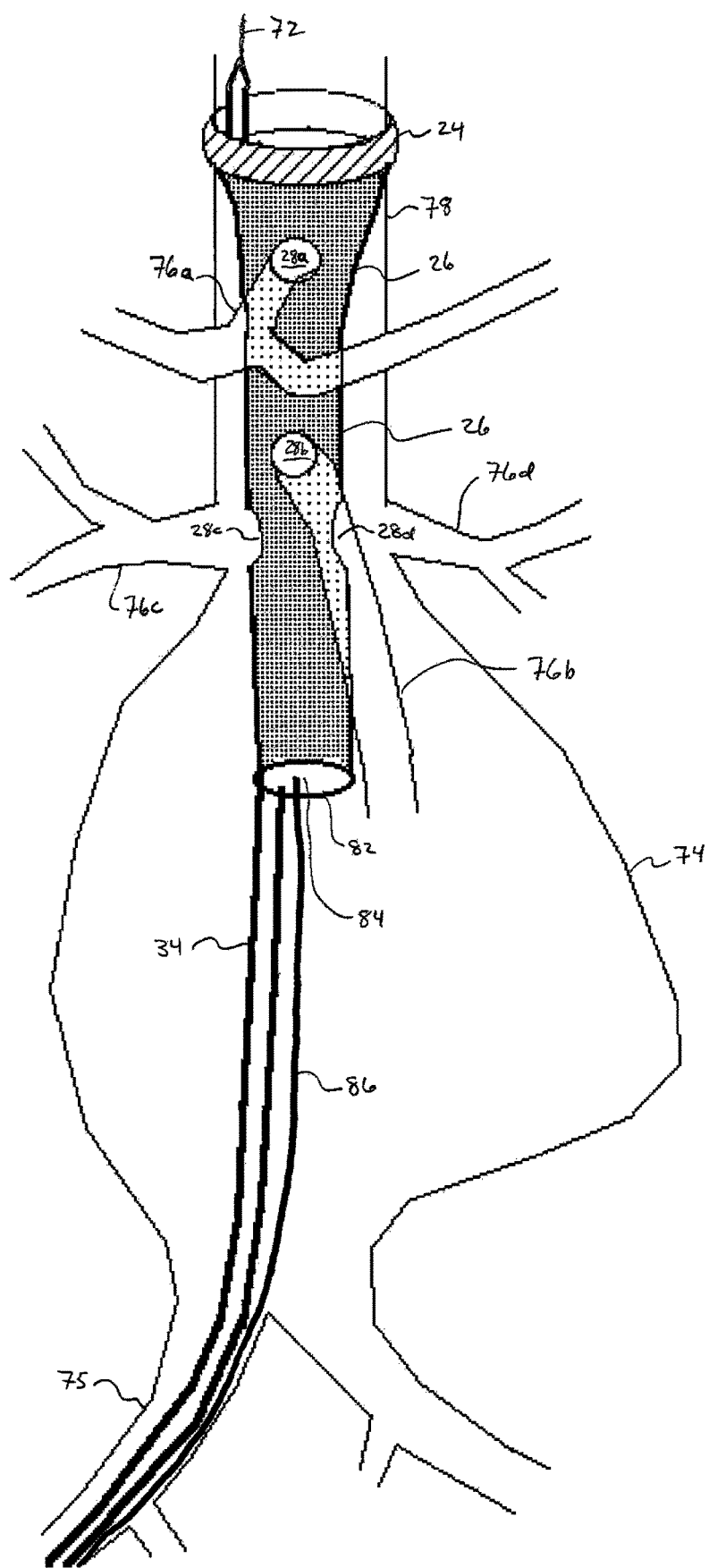

Once guide wire 72 is in place, catheter 34, with the aortic router device collapsed over it, is advanced along guide wire 72 so as to become positioned at the desired location within the artery, as illustrated in FIG. 4A. As illustrated in FIGS. 4A and 4B, the desired location positions the fenestrations 28a-28d in alignment with the branch arteries proximal to the aneurysm 76a-76d.

As shown in FIG. 4B, the cuff 24 is next inflated using the technique described above so as to circumferentially engage the interior surface of the aortic wall 78. As a result, the inflatable cuff achieves both fixation and sealing to the interior surface of the aortic wall.

Because the aortic router may be positioned without causing damage to the surrounding tissue, it may be deflated and repositioned if the original position is not optimal. More specifically, after the cuff 24 has been inflated so that the router device is affixed to the aortic wall without penetration, the position of the cuff is examined fluoroscopically to determine if it is optimal. If not, the cuff may be deflated, repositioned and then re-inflated. When the optimal position is achieved, the cuff preferably is finally inflated with a hardening agent.

When this stage of the procedure has been completed, the catheter 34 is disconnected from the inflatable cuff 24 so that the catheter may be removed from the artery. The valve of the cuff described above allows the inflation stem of the catheter to be removed from the cuff inflation port so that the cuff is sealed in an inflated condition.

Once properly positioned, the router device allows the placement of a commercially available endograft in an otherwise untreatable aneurysm. In the example presented below, the introduction of the endograft precedes the introduction of the covered stent branches. It is to be understood, however, that the method of the present invention could be performed instead in reverse order (covered stent branches introduced before the endograft).

Figure 4C:
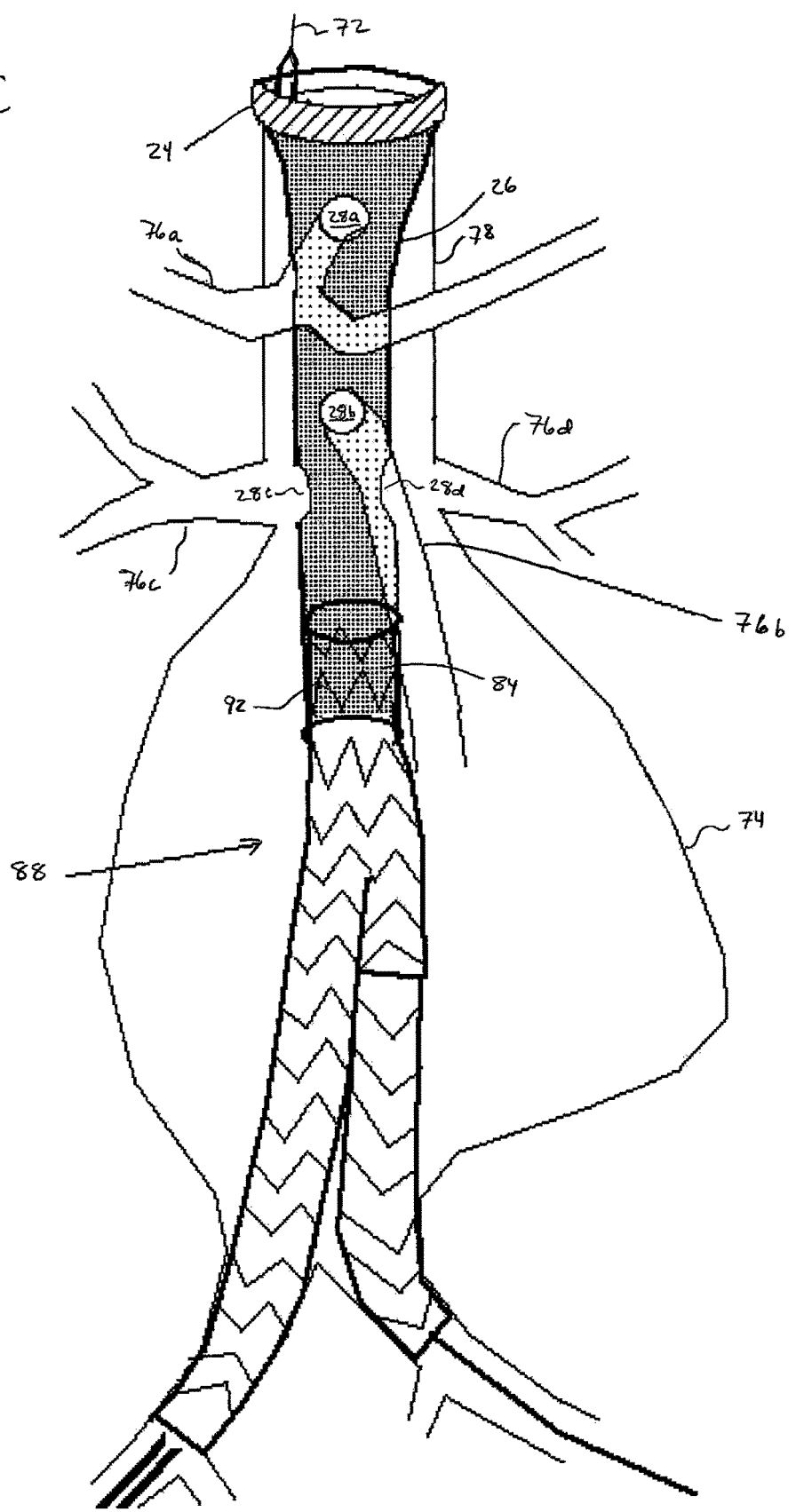

With reference to FIGS. 4B and 4C, the distal end 82 of the tubular graft 26 of the router device, in its preferred embodiment, is open ended, so as to form distal lumen 84, and tapered to a diameter less than that of the endograft to be introduced for aneurysm repair (see also FIG. 1). The distal end 82 of the router device is cannulated during the course of the procedure with a second guidewire, indicated at 86 in FIG. 4B, and one of the commercially available endografts, indicated in general at 88 in FIG. 4C, is advanced over the second guidewire and the metallic exoskeleton 92 of the endograft deployed within the distal lumen 84, as illustrated in FIG. 4C. The original guidewire 72 may alternatively be used to insert and position the endograft. Because the graft material for the distal end of the tubular graft is of a slightly smaller diameter than the commercial endograft, and is preferably tapered to successively smaller diameter as it extends distal, the metallic exoskeleton of the deployed endograft forms a frictional fit seal with essentially no risk for distal migration. Again, the endograft deployment may take place before the branch covered stents are introduced, but may also be done afterwards.

It is important to note that at no time is flow to branch vessels 76a-76d interrupted during deployment of the router and the endograft device. Hence, the router device may actually be placed during an earlier procedure, and the introduction of the endograft may be accomplished during a later procedure, if the patient cannot tolerate a more prolonged procedure or the physician prefers for whatever reason to stage the procedure.

Once the cuff 24 has been inflated with a hardening agent and secured to the wall, the fenestrations 28a-28d (FIGS. 4B and 4C) are cannulated separately, and bridging small covered stents, illustrated at 96a-96d in FIGS. 4D and 5A-5C, are deployed. Suitable stents are well known in the art and are commercially available from, for example, W.L. Gore & Associates Inc. of Flagstaff, Ariz., C.R. Bard, Inc. of Murray Hill, N.J. and Atrium Medical Corporation of Hudson, N.Y. As is known in the art, such stents are initially introduced into a vessel in a collapsed condition and then expand for affixing to the interior wall of a vessel or other structure. Furthermore, the stent of commonly owned U.S. Pat. No. 6,007,575 may be used.

As illustrated in FIG. 5A, guidewires 102c and 102d are inserted into the patient's renal arteries 76c and 76d and the stents 96c and 96d are moved, in a collapsed condition, over the guidewire and into position within the corresponding fenestrations 28c and 28d. As illustrated in FIG. 5B, the stents 96c and 96d are then expanded so that they engage the fenestrations 28c and 28d (FIGS. 4B, 4C and 5A) in an interference fit fashion, and are thus secured to and within, the fenestrations of the tubular graft 26 of the router device. The guidewires may them be removed from the renal arteries, as illustrated in FIG. 5C. Stents 96a and 96b of FIG. 4D may be positioned within, and attached to, fenestrations 28a and 28b of the tubular graft 26 of the router device in a similar fashion. Alternative methods and arrangements known in the art may be used to attach the stents to the fenestrations of the tubular graft in place of the method and arrangement described above.

Flow through the aorta is maintained throughout the process. Thus, even in procedures of long duration, and as noted previously, flow is maintained to all branch vessels. The absence of the endoskeleton in the router device allows for the more easy tapering of the tubular graft immediately below the level of the cuff. This taper to a smaller diameter creates a slightly wider gap between the tubular graft of the router device and the branch vessel origins. This is extremely beneficial as it allows cannulation of sidebranches even if the alignment of the fenestration is suboptimal. This greatly reduces the precision required in the deployment of the device, and greatly increases the ease with which the branch vessels may be cannulated via the corresponding fenestrations.

As illustrated in FIG. 4D, the placement of the covered stents 96a-96d through the fenestrations of the tubular graft 26 of the router device to create branch connections, in combination with the attachment of the endograft 88 to the distal end of the router device, creates a sealed continuous inner lumen which effectively excludes the aneurysm 74 from the circulation.

Figure 6B:
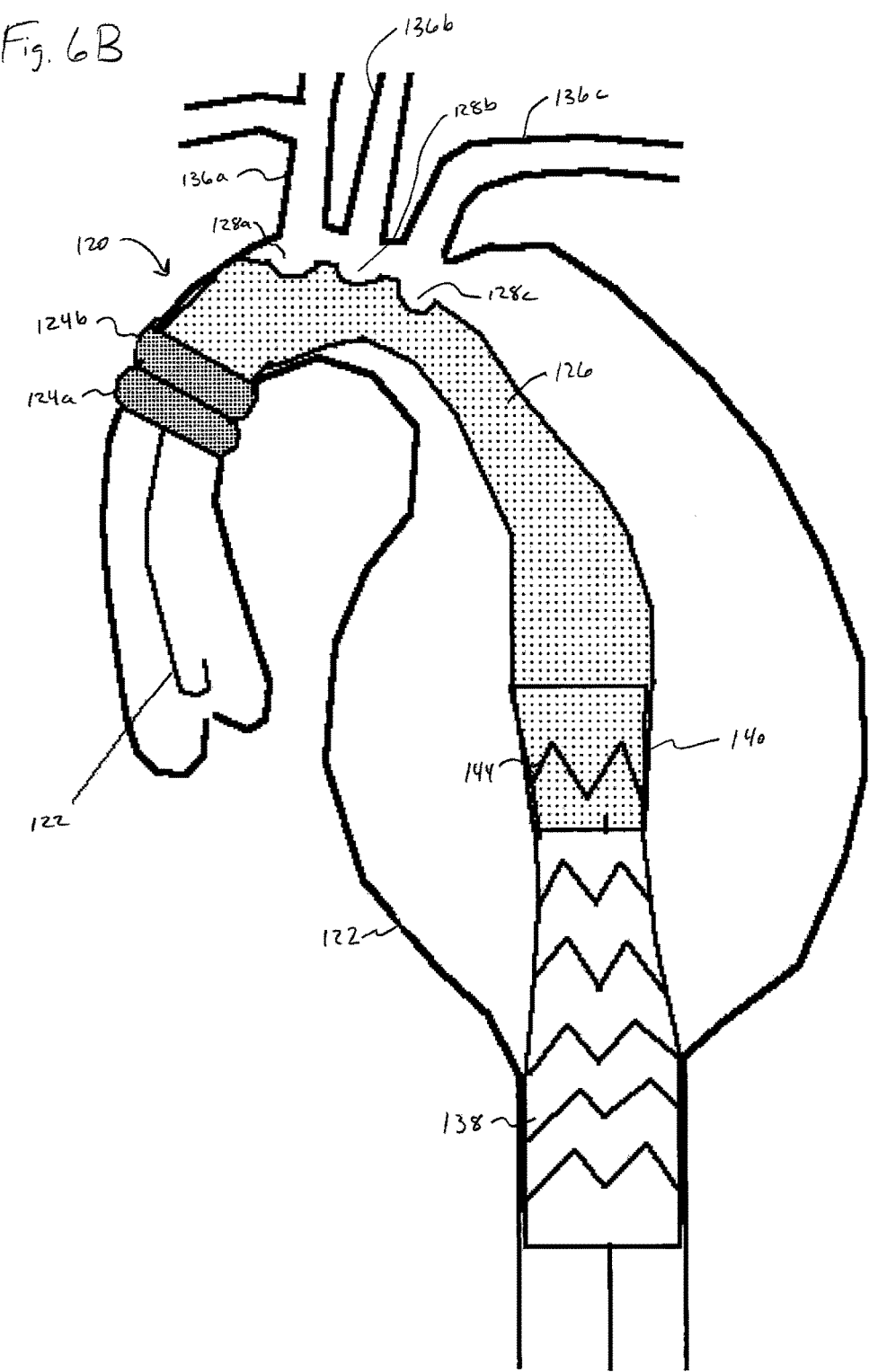
Figure 6C:
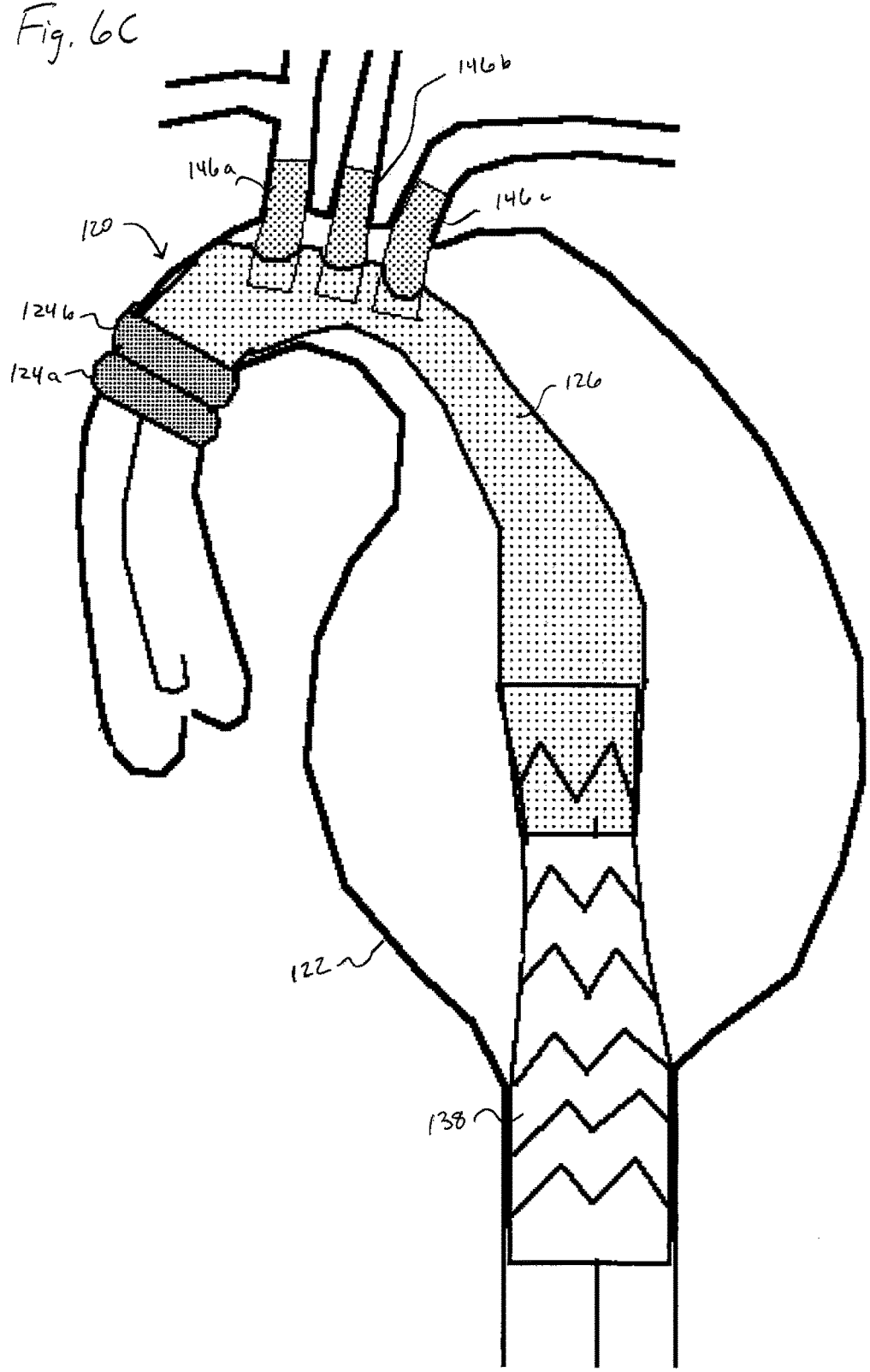

FIGS. 6A-6C illustrate the steps to be performed in deploying an embodiment of the router device, indicated in general at 120, to treat a thoracic aortic aneurysm 122 in the accordance with an embodiment of the method of the present invention.

The router device 120 features a construction similar to the router device 20 of FIGS. 1-5C, the exception being that it features two inflatable cuffs 124a and 124b attached to the proximal end of the tubular graft 126. Each cuff features its own inflation port and valve, each of the type illustrated at 39 and 37 in FIGS. 3A and 3B, and the catheter features two inflation stems (each of the type illustrated at 61 in FIGS. 3A and 3B) that are in fluid communication with the catheter inflation lumen and that removably engage the inflation ports of the two cuffs.

The router device is initially inserted into the thoracic artery in a collapsed condition over a catheter using a guidewire 122, as described above with respect to FIGS. 4A and 4B.

The catheter, with the aortic router device collapsed over it, is advanced along guide wire 122 so as to become positioned at the desired location within the artery. As illustrated in FIG. 6A, the cuffs 124a and 124b are inflated with the router device in the desired location, that is, with the fenestrations 128a-128c, in alignment with the branch arteries proximal to the aneurysm 136a-136c. As described above with respect to FIG. 4B, the catheter is removed from the artery when the router device has been optimally positioned and the cuffs inflated with a hardening agent.

As illustrated in FIG. 6B, once the router device 120 is properly positioned, its tapered distal end 140 is cannulated and a commercially available endograft 138 is attached therein by way of the endograft's metallic exoskeleton 144. In the example presented below, the introduction of the endograft precedes the introduction of the covered stent branches. It is to be understood, however, that the process could be performed instead in reverse order (covered stent branches introduced before the endograft).

Once the cuffs 124a and 124b have been inflated with a hardening agent and secured to the wall, and either before or after attachment of the endograft device 138, the fenestrations 128a-128c are cannulated separately, and bridging small covered stents, illustrated at 146a-146c in FIG. 6C, are deployed therein, as described above with respect to FIGS. 5A-5C.

As illustrated in FIG. 6C, the placement of the covered stents 146a-146c through the fenestrations 128a-128c of the tubular graft 126 of the router device to create branch connections, in combination with the attachment of the endograft 138 to the distal end of the router device, creates a sealed continuous inner lumen which effectively excludes the aneurysm 122 from the circulation.

While the preferred embodiments of the invention, as described above, use one or more inflatable cuffs as the attachment mechanism or arrangement for affixing the device to the interior surface of the vessel, other embodiments for the attachment mechanism are feasible. A self expanding stent arrangement, well known in the art, may be attached to the proximal end of the graft and deployed through a standard sheath introducer. Further, such a self expanding stent arrangement, in order to maintain the advantage detailed above of repositionability, may incorporate a constraining wire arrangement that allows partial deployment of the self expanding stent to a diameter less than its fully expanded state, or a diameter less than that of the adjacent aorta. By this arrangement, the graft may be repositioned prior to the removal of the constraining wire so as to best align the fenestrations 28a-d with the branch vessels 76a-d. In another embodiment, the graft 26 is deployed initially in the absence of the accompanying attachment mechanism, with the proximal end 24 free floating in the arterial lumen and expanded against the adjacent wall by the pressure of the flowing blood. The attachment of graft 26 to the deployment catheter 34 is maintained through a removable binding mechanism such as a suture, such that movement and rotation of the deployment catheter 34 will still effect the desired change in position in graft 26 to optimize alignment of fenestrations 28a-d (or 128a-c) with branch vessels 76-a-d (or 136 a-c). In this embodiment, the preferred sequence would then be introduction of covered stents 96a-d (or 146a-c), aiding in the fixation of the graft 26 (or 126) which until that point will not have undergone definitive fixation. Subsequently, an inflatable cuff element as embodied in 24 or 124 may be introduced and deployed separately, achieving such fixations. Similarly, a self expanding stent, as exists in the art, or a balloon expandable stent, as also exists in the art, may be introduced and deployed at the proximal end of graft 26 or 126 to achieve fixation. Other possible strategies for fixation of the proximal end may be possible as well.

The router device of the present invention may optionally be provided with a malleable portion circumferentially surrounding each fenestration, as indicated in FIG. 7 where the ring-shaped malleable portion 152 surrounds fenestration 154. As described previously with regard to router device 20 of FIG. 1 and router device 120 of FIGS. 6A-6C, the fenestration 154 is formed in the wall 156 of the tubular graft of the router device.

The malleable portion 152 is preferably constructed from a variety of synthetic plastics, such as urethane based materials, which are bioinert, but other malleable materials known in the art may be used instead. The malleable material itself may be encapsulated within an enveloping synthetic material, which, in the preferred embodiment, is composed of the same synthetic material as the tubular graft 156 (or 26 and 126 in FIGS. 1 and 6A, respectively) itself. This limits the possibility of any fragmentation of the malleable material during the process of compression by the branch covered stent.

Figure 8A:
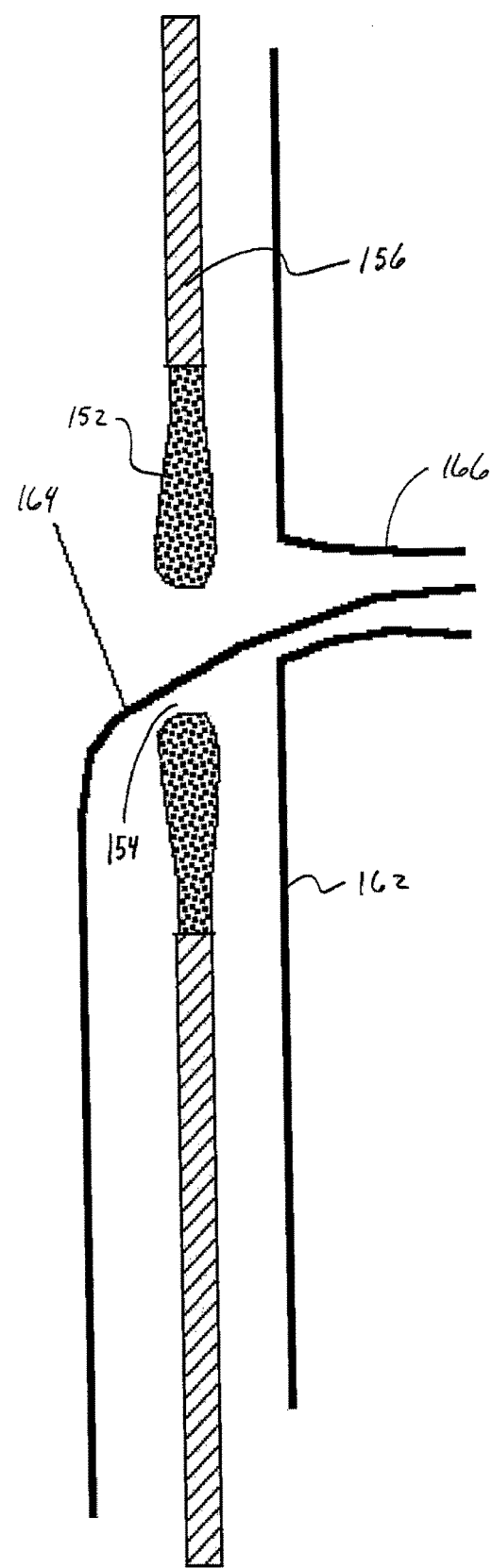
Figure 8B:
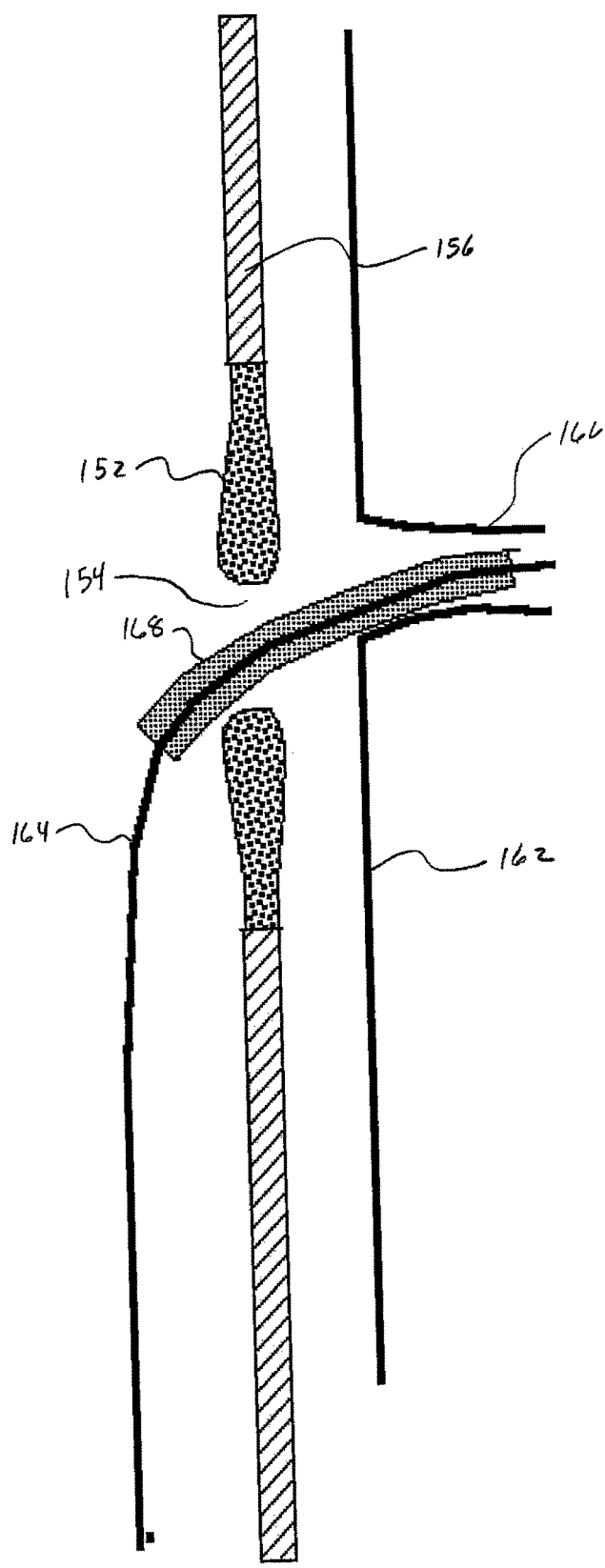
Figure 9:
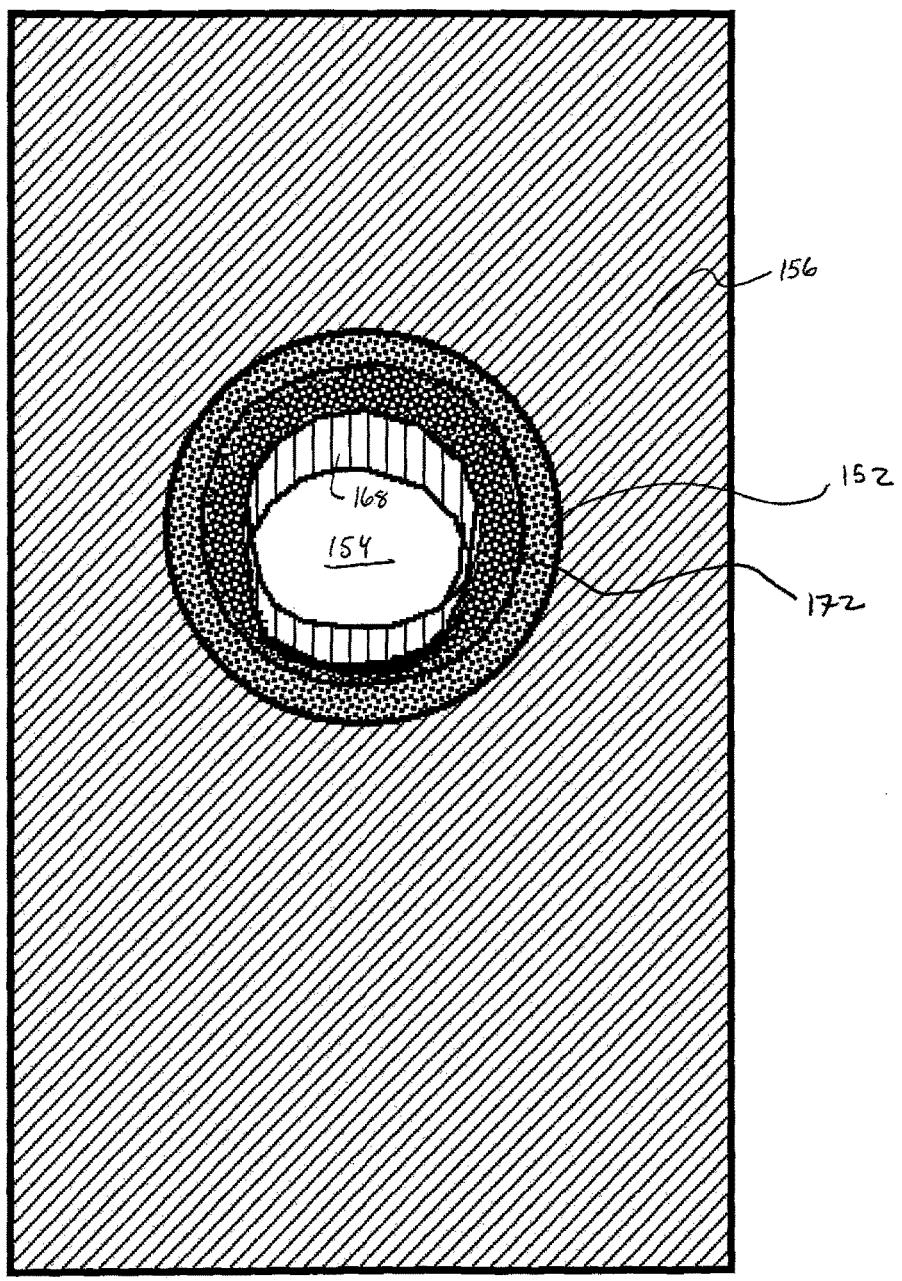
FIG. 9 is a side elevational view of a tubular graft wall of FIG. 8C taken in the direction of arrow 9 in FIG. 8C.

As illustrated in FIG. 8A, after the router device featuring tubular graft wall 156 is positioned within a tubular vessel, such as aorta 162, a guidewire 164 is passed through a branch artery 166 and fenestration 154. As illustrated in FIG. 8B, a stent 168 in a collapsed condition is then passed over the guidewire 164 through branch artery 166 and into the fenestration 154. With reference to FIG. 8C, the stent 168 is then expanded radially so as to engage the malleable portion 152 surrounding the fenestration. As a result, the malleable portion 152 deforms to form a deformed portion 172 which is securely sealed against the exterior surface of the stent, as illustrated in FIGS. 8C and 9.

The aortic router device and method described above therefore offers several advantages over the prior art. It allows the construction of the body of the device to be free of a metallic endoskeleton and thus conforms well to the aorta, even when there is significant tortuosity of the vessel, or angulation of the vessel segments. Second, the inflatable cuff, through use of a valve, can be inflated and deflated so that repositioning can be undertaken. Optimal positioning can be achieved before final inflation of the cuff, with a hardening agent, is performed. Flow through the aorta is maintained throughout the installation of the router device and the stents so that, even in procedures of long duration, flow is maintained to all branch vessels. The absence of the endoskeleton allows for the more easy tapering of the graft material immediately below the level of the cuff. This taper to a smaller diameter creates a slightly wider gap between the device and the branch vessel origins which permits cannulation of sidebranches, even if the alignment of the fenestration is suboptimal. The absence of the metal endoskeleton also allows the overall size of the aortic router device to be reduced, and hence there is the potential to introduce it through a smaller catheter delivery system.

The router device of the present invention may be constructed in many different sizes and shapes. The only criterion which must be met is that the inflatable cuff must be of an appropriate width and diameter so that the device, branch stents and endografts are fully supported within the tubular structure by the inflatable cuff. As a result, not only can the invention be practiced in small structures, such as the vascular system, but also, the device may be affixed within much larger structures, such as the excretory system.

While the preferred embodiments of the invention have been shown and described, it will be apparent to those skilled in the art that changes and modifications may be made therein without departing from the spirit of the invention, the scope of which is defined by the appended claims.

What is claimed is:

1. A router device for repairing a tubular vessel of a patient, where the tubular vessel is joined to at least one branch vessel, the router device comprising:
    a) a single wall and skeleton-free tubular graft having a proximal end and a distal end and at least one unobstructed fenestration formed therein before deployment in the patient, said fenestration adapted to receive and affix a stent, and a malleable annulus formed in a side of said tubular graft wherein the inner diameter of the annulus defines the fenestration and where the annulus inner diameter when deformed has a portion adjacent to the stent with a greater width than the outer diameter of the annulus and said fenestration sized and positioned to generally align with the branch vessel;
    b) said distal end of the tubular graft having a diameter less than a diameter of the proximal end, and said single wall of the tubular graft including a tapered portion between the proximal and distal ends, wherein said fenestration is positioned within the tapered portion;
    c) a cylindrical element including an outer surface that is adapted to be juxtaposed circumferentially to an interior surface of the tubular vessel so as to releasably affix the proximal end of the tubular graft to an interior surface of the tubular vessel so that the tubular graft may be repositioned within the tubular vessel of the patient; and
    d) said distal end of the tubular graft configured so as to be suspended within an aneurysm formed in the tubular vessel when the proximal end of the tubular graft is affixed to the interior surface of the tubular vessel by the cylindrical element.

2. The router device of claim 1 wherein the cylindrical element includes an inflatable cuff.

3. The router device of claim 2 wherein the inflatable cuff includes a friction-enhancing outer surface.

4. The router device of claim 3 wherein the friction-enhancing outer surface includes a material that promotes tissue ingrowth.

5. The router device of claim 1 further comprising a deployment catheter having a guidewire lumen and an inflation lumen in fluid communication with the inflatable cuff.

6. The router device of claim 5 wherein the inflatable cuff includes an inflation port having a valve and the deployment catheter includes an inflation stem removably engaging the inflation port and valve.

7. The router device of claim 6 wherein the valve includes a mitre valve and a breakaway valve.

8. The router device of claim 5 further comprising an inflation syringe containing a supply of inflation material, said inflation syringe in fluid communication with the inflation lumen of the deployment catheter.

9. The router device of claim 1 wherein the tubular graft includes a plurality of inflatable cuffs.

10. The router device of claim 1 wherein the distal end of the tubular graft is adapted to receive an endograft.

11. The router device of claim 1 wherein the tubular graft is constructed of a biocompatible synthetic material.

12. The router device of claim 1 wherein said annulus has a first larger circumference joined by a material to a second smaller circumference adjacent and surrounding the fenestration, said annulus formed of a material different from a material of the single wall of the tubular graft and configured so as to deform due to form a deformed portion having a final circumference in size between the first and second circumferences and that engages an exterior surface of the stent which seals against the exterior surface of a stent positioned therein.

13. The router device of claim 12 wherein the annulus is constructed from a bioinert synthetic plastic.

14. The router device of claim 1 wherein the tubular graft is tapered so as to have a generally decreasing diameter when moving from the proximal end to the distal end.

15. A system for repairing a tubular vessel of a patient, where the tubular vessel is joined to at least one branch vessel, the system comprising:
    a) a single wall and skeleton-free tubular graft having a proximal end and a distal end and at least one unobstructed fenestration formed therein before deployment in the patient, said fenestration sized and positioned to generally align with the branch vessel said tubular graft further comprising a deformable annulus formed in the side of the graft and disposed about the fenestration;

b) a stent secured within the fenestration and adapted to engage an interior surface of the branch vessel where the inner diameter of the annulus when deformed has a portion adjacent to the stent with a greater width than the outer diameter of the annulus;

c) said distal end of the tubular graft having a diameter less than a diameter of the proximal end of tubular graft, and said single wall of the tubular graft including a tapered portion between the proximal and distal ends, wherein said fenestration is positioned within the tapered portion;

d) a cylindrical element including an outer surface that is adapted to be juxtaposed circumferentially to an interior surface of the tubular vessel so as to releasably affix the proximal end of the tubular graft to an interior surface of the tubular vessel so that the tubular graft may be repositioned within the tubular vessel of the patient;

e) said distal end of the tubular graft configured so as to be suspended within an aneurysm formed in the tubular vessel when the proximal end of the tubular graft is affixed to the interior surface of the tubular vessel by the cylindrical element.

16. The system of claim 15 further comprising an endograft attached to the distal end of the tubular graft.

17. The system of claim 15 wherein the cylindrical element includes an inflatable cuff.

18. The system of claim 17 wherein the inflatable cuff includes a friction-enhancing outer surface.

19. The system of claim 18 wherein the friction-enhancing outer surface includes a material that promotes tissue ingrowth.

20. The system of claim 17 further comprising a deployment catheter having a guidewire lumen and an inflation lumen in fluid communication with the inflatable cuff.

21. The system of claim 20 wherein the inflatable cuff includes an inflation port having a valve and the deployment catheter includes an inflation stem in fluid communication with the inflation lumen and removeably engaging the inflation port and valve.

22. The system of claim 21 wherein the valve includes a mitre valve and a breakaway valve.

23. The system of claim 20 further comprising an inflation syringe containing a supply of inflation material, said inflation syringe in fluid communication with the inflation lumen of the deployment catheter.

24. The system of claim 15 wherein the cylindrical element includes a plurality of inflatable cuffs.

25. The system of claim 15 wherein the tubular graft is constructed of a biocompatible synthetic material.

26. The system of claim 15 wherein the annulus has a first larger circumference joined by a material to a second smaller circumference adjacent and surrounding the fenestration, said annulus formed of a material different from a material of the single wall of the tubular graft and configured so as to deform to form a portion which seals against an exterior surface of a stent positioned therein.

27. The router device of claim 26 wherein the annulus is constructed from a bioinert synthetic plastic.

28. The router device of claim 15 wherein the tubular graft is tapered so as to have a generally decreasing diameter when moving from the proximal end to the distal end.

29. A method for repairing a tubular vessel of a patient, where the tubular vessel is joined to at least one branch vessel, the method comprising the steps of:

a) providing a router device including a single wall and skeleton-free tubular graft having a proximal end and a distal end with a tapered portion between the proximal and distal ends, an inflatable cuff positioned at the proximal end of the tubular graft and at least one unobstructed fenestration formed therein before deployment in the patient, said fenestration sized and positioned to generally align with the branch vessel;

b) inserting a first guidewire into the tubular vessel;

c) collapsing the router device on a deployment catheter;

d) advancing the deployment catheter along the first guidewire into a position where the fenestration is generally aligned with the branch vessel;

e) circumferentially engaging an interior surface of the tubular vessel solely by inflating the inflatable cuff so that the distal end of the tubular graft is freely suspended within an aneurysm formed in the tubular vessel, the distal end capable of limited movement to maintain access to the fenestration in alignment with the branch vessel;

f) examining a position of the tubular graft within the tubular vessel;

g) disengaging the proximal end of the tubular graft from the interior wall of the tubular vessel by deflating the inflatable cuff;

h) repositioning the tubular graft within the tubular vessel;

i) circumferentially engaging an interior surface of the tubular vessel solely by inflating the inflatable cuff so that the distal end of the tubular graft is suspended within the tubular vessel;

j) inserting a second guidewire into the branch vessel;

k) advancing a stent in a collapsed condition along the second guidewire through the branch vessel and into the fenestration to engage an annulus disposed about the fenestration, said annulus having a first circumference defining the fenestration; and l) expanding the stent to affix it to the fenestration and an interior surface of the branch vessel by deforming the annulus to a second larger circumference about the fenestration and create a sealed region about said stent and when deformed the portion adjacent to the stent has a greater width than the outer diameter of the annulus.

30. The method of claim 29 further comprising the step of attaching an endograft device to the distal end of the tubular graft.

31. The method of claim 29 further comprising the step of performing a computed tomography scan on the patient to determine the proper location of the fenestrations prior to providing the router device of step a).

32. The method of claim 29 wherein the vessel is an abdominal aorta having an aneurysm.

33. The method of claim 29 wherein the vessel is a thoracic aorta having an aneurysm.

34. The method of claim 29 wherein the tubular vessel has an aneurysm downstream of the branched vessel and step d) includes advancing the deployment catheter along the first guidewire into a position where the proximal end of the tubular graft is positioned upstream of the branch vessel so that the fenestration is generally aligned with the branch vessel and the distal end is suspended within the aneurysm.

* * * * *